(12) United States Patent
Kim et al.

(10) Patent No.: US 9,837,934 B2
(45) Date of Patent: Dec. 5, 2017

(54) FIBROUS TRIBOELECTRIC GENERATOR AND ELECTRONIC STIMULATOR USING THE FIBROUS TRIBOELECTRIC GENERATOR AND CLOTHES USING THE ELECTRONIC STIMULATOR

(71) Applicant: RESEARCH & BUSINESS FOUNDATION SUNGKYUNKWAN UNIVERSITY, Suwon-si (KR)

(72) Inventors: Sang-Woo Kim, Yongin-si (KR); Ju-Hyuck Lee, Suwon-si (KR); Wanchul Seung, Yongin-si (KR); Hanjun Ryu, Suwon-si (KR); Hong-Joon Yoon, Goyang-si (KR); Keun Young Lee, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/951,809

(22) Filed: Nov. 25, 2015

(65) Prior Publication Data

US 2016/0156282 A1    Jun. 2, 2016

(30) Foreign Application Priority Data

Nov. 28, 2014   (KR) .................. 10-2014-0168844

(51) Int. Cl.
| | | |
|---|---|---|
| A61N 1/00 | (2006.01) |
| H02N 1/04 | (2006.01) |
| A61N 1/378 | (2006.01) |
| A61N 1/04 | (2006.01) |
| A61N 1/36 | (2006.01) |

(52) U.S. Cl.
CPC ............. *H02N 1/04* (2013.01); *A61N 1/0484* (2013.01); *A61N 1/3787* (2013.01); *A61N 1/36014* (2013.01)

(58) Field of Classification Search
CPC ....... H02N 1/04; A61N 1/0484; A61N 1/3787
See application file for complete search history.

(56) References Cited

U.S. PATENT DOCUMENTS

2015/0061460 A1*  3/2015  Bae .................... H02N 1/04
                                                310/310
2015/0321000 A1*  11/2015  Rosenbluth .......... A61N 1/0492
                                                607/48

* cited by examiner

*Primary Examiner* — Scott Getzow
(74) *Attorney, Agent, or Firm* — NSIP Law

(57) ABSTRACT

Disclosed is a fibrous triboelectric generator. The fibrous triboelectric includes a first textile; a first electrode layer that is formed on a surface of the first textile; a friction layer that is formed on a surface of the first electrode layer and is able to be electrically charged by friction; and a second electrode layer that is able to undergo friction with the friction layer.

16 Claims, 8 Drawing Sheets

POCKET ON INNER SURFACE OF SLEEVE

POCKET ON OUTER SURFACE OF SLEEVE

FIBROUS TRIBOELECTRIC GENERATOR AND ELECTRONIC STIMULATOR USING THE FIBROUS TRIBOELECTRIC GENERATOR AND CLOTHES USING THE ELECTRONIC STIMULATOR

CROSS-REFERENCE TO RELATED APPLICATION

This application claims priority to and the benefit of Korean Patent Application No. 2014-0168844, filed on Nov. 28, 2014, the disclosure of which is incorporated herein by reference in its entirety.

BACKGROUND

1. Field of the Invention

The present invention relates to an electricity generating device using triboelectricity, and more particularly, to an electronic stimulator that is equipped with the fibrous triboelectric generator and uses triboelectricity, and to a clothes that generates electricity and is equipped with the electronic stimulator that uses the fibrous triboelectric generator and triboelectricity.

2. Discussion of Related Art

Electronic stimulators, which are used in a variety of applications such as in the treatment or rehabilitation of human bodies, are installed in physiotherapy clinics of hospitals and depend on the power supplied from an external source for operation. Such electric stimulators are generally expensive and always require power supply from a built-in battery or an external power source.

In addition, the user (i.e. patient) needs to personally visit the hospital for electrical stimulation therapies or personally purchase and install expensive equipment in his or her own house for use, thus having a burden of spending a certain period of time at a defined place for treatment. In other words, conventionally, there have always been spatial and temporal constraints in using the electronic stimulator.

Hence, the present inventors have come to develop, by introducing a device capable of triboelectricity generation to a conventional electronic stimulator, a fibrous triboelectric generator that is capable of electrical stimulation even without power supply from an external source and of frequent and sustained electrical stimulation even as being moved, an electronic stimulator using the same, and a clothes using such an electronic stimulator.

SUMMARY OF THE INVENTION

The present invention is directed to providing a fibrous triboelectric generator that can generate triboelectricity.

In addition, the present invention is directed to providing an electronic stimulator that includes the fibrous triboelectric generator—which can generate triboelectricity—and uses triboelectricity.

Furthermore, the present invention is directed to providing a clothes for triboelectricity generation, which is capable of generating triboelectricity using the fibrous triboelectric generator and of electrical stimulation using the generated triboelectricity.

According to an exemplary embodiment of the present invention, the fibrous triboelectric generator may include a first textile; a first electrode layer that is formed on a surface of the above first textile; a friction layer that is formed on a surface of the above first electrode layer and can be electrically charged by friction; and a second electrode layer that can undergo friction with the above friction layer.

In one exemplary embodiment, the above friction layer may consist of a nonconductive polymer and has a surface with a concavo-convex structure.

In one exemplary embodiment, the above surface of the friction layer may include a plurality of first linear protrusions that are extended along a first direction and a plurality of second linear protrusions that are extended along a second direction which is different from the first direction.

In one exemplary embodiment, the above surface of the friction layer may include a plurality of protrusions that are spaced apart from one another.

In one exemplary embodiment, the above friction layer may include a metal oxide that protrudes from a surface of the above first electrode layer; and a coating layer that coats a surface of the above metal oxide and the surface of the above first electrode layer.

In one exemplary embodiment, the above metal oxide may be zinc oxide (ZnO).

In one exemplary embodiment, the above coating layer may consist of a nonconductive polymer.

In one exemplary embodiment, the above nonconductive polymer may consist of one or more selected from the group consisting of polydimethylsiloxane (PDMS), polytetrafluoroethylene (PTFE), and polyvinylidene fluoride (PVDF).

According to an exemplary embodiment of the present invention, the fibrous triboelectric generator may further include a second textile that is placed on an side of the above first textile, with the above second electrode layer positioned therebetween, where the above second electrode layer may be formed on a surface of the above second textile.

According to an exemplary embodiment of the present invention, the electronic stimulator using triboelectricity may include a first textile; a first electrode layer that is formed on a surface of the above first textile; a friction layer that is formed on a surface of the above first electrode layer, has a surface with a concavo-convex structure, and can be electrically charged by friction; a second electrode layer that can undergo friction with the above friction layer; a first pad that is electrically connected with the above first electrode layer; and a second pad that is electrically connected with the above second electrode layer.

In one exemplary embodiment, the above friction layer may consist of a nonconductive polymer.

In one exemplary embodiment, the above friction layer may include a metal oxide that protrudes from a surface of the above first electrode layer; and a coating layer that coats a surface of the above metal oxide and the surface of the above first electrode layer.

In one exemplary embodiment, the above metal oxide may be ZnO.

According to an exemplary embodiment of the present invention, the electronic stimulator using triboelectricity may further include a second textile that is placed on an side of the above first textile, with the above second electrode layer positioned therebetween, where the above second electrode layer may be formed on a surface of the above second textile.

According to an exemplary embodiment of the present invention, a clothes that generates triboelectricity may include a first textile and a second textile that are disposed to face each other; a first electrode layer that is formed on a surface of the above first textile on a facing side of the above second textile; a friction layer that coats the above first electrode layer, has a surface with a concavo-convex structure, and can be electrically charged by friction; and a second electrode layer that is formed on a surface of the above second textile on a facing side of the above first textile, and can undergo friction with the above friction layer.

According to an exemplary embodiment of the present invention, the clothes that generates triboelectricity may further include a first pad that is electrically connected with the above first electrode layer; and a second pad that is electrically connected with the above second electrode layer. The triboelectricity produced using the first pad and the second pad can enable electrical stimulation.

The present invention as described above enables the control of the magnitudes of the generated voltage and electric current by changing the magnitude of an external force.

The present invention enables the variation of the magnitudes of the generated voltage and electric current by stacking fibrous triboelectric generators.

The present invention uses textiles that consist of a fibrous polymer and thus enables an application in a clothes.

When the fibrous triboelectric generator is applied in a clothes, the user can be continuously treated by frequently applying electrical stimulation to an affected area even without requiring a particular power supply. In addition, frequent electrical stimulation is possible without temporal and spatial constraints.

The present invention enables, by suitably selecting a material capable of generating triboelectricity, the production of a clothes that can provide customized electrical stimulation through the variation of the magnitudes of voltage and electric current of triboelectricity to be appropriate for the circumstances.

The present invention enables the generation of triboelectricity using friction that can be easily generated in our daily lives and thus enables a meaningful use of triboelectricity that usually goes meaninglessly wasted.

DETAILED DESCRIPTION OF EXEMPLARY EMBODIMENTS

The present invention may have various exemplary embodiments and various modifications, and thus only particular embodiments will be presented in a detailed description section and exemplified with reference to drawings. However, this is not intended to limit the present invention to one or more specific embodiments, and it should be understood that all modifications, equivalents and substitutes are included in the spirit and scope of the present invention.

Hereinafter, a few selected exemplary embodiments of the present invention will be described in detail with reference to accompanying drawings. In the drawings, like reference numerals refer to like elements.

Figure 1:
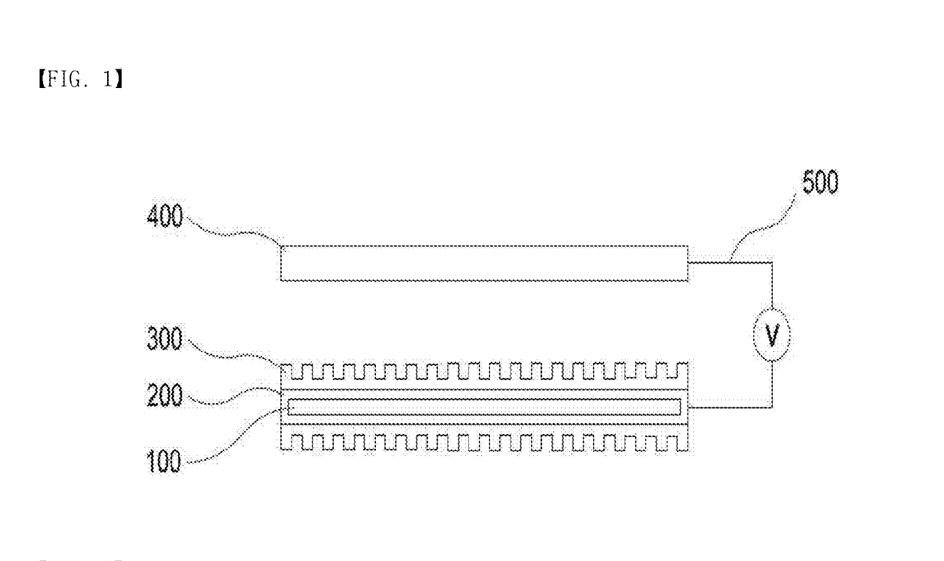
FIG. 1 is a cross-sectional view of a fibrous triboelectric generator according to an exemplary embodiment of the present invention.
Figure 2:
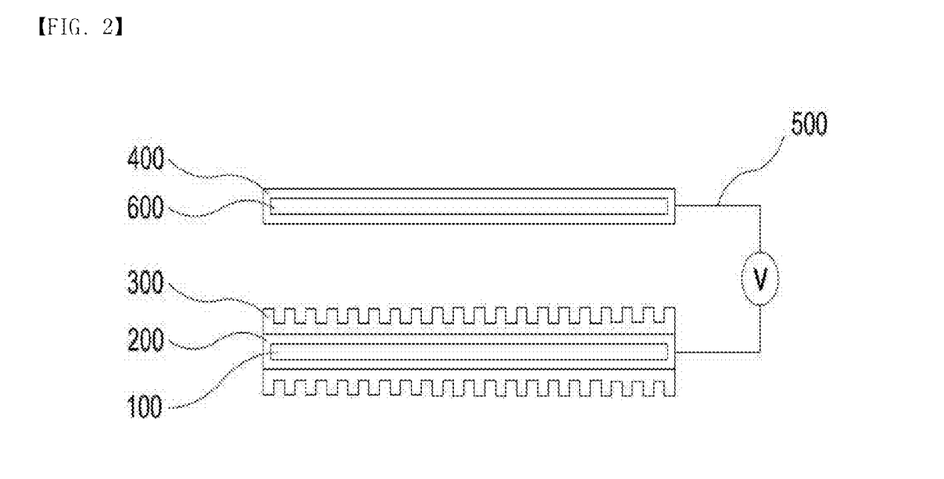
FIG. 2 is a cross-sectional view of a fibrous triboelectric generator according to another exemplary embodiment of the present invention.
Figure 3A:
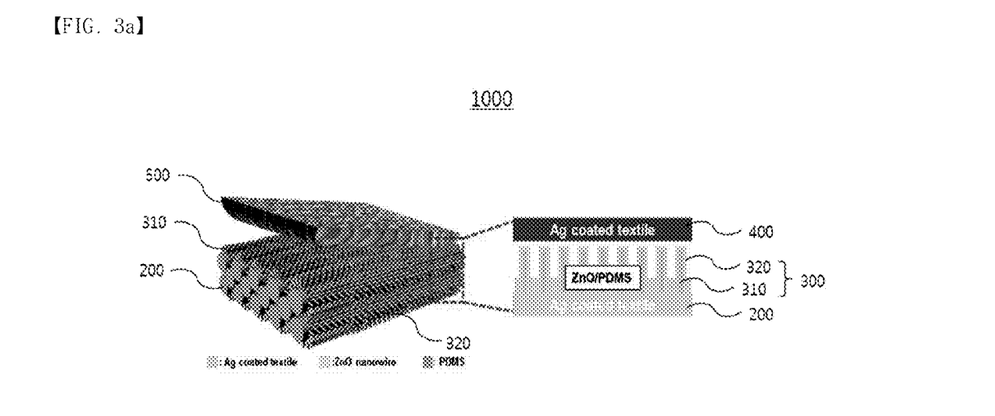
FIG. 3A is a schematic view of a fibrous triboelectric generator according to still another exemplary embodiment of the present invention.
Figure 3B:
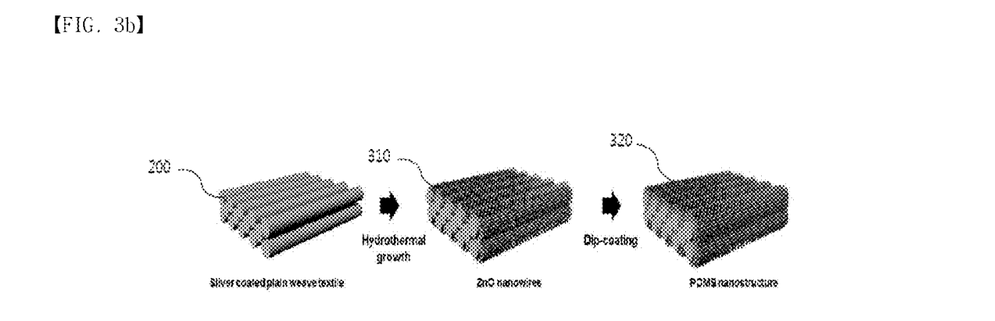
FIG. 3B is a diagram that describes the formation of a friction layer of the fibrous triboelectric generator of FIG. 3A.
Figure 4:
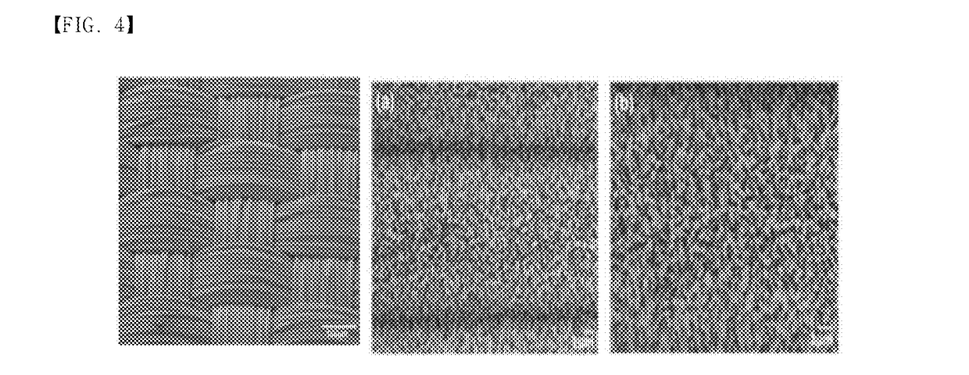
FIG. 4 is a field-emission scanning electron microscopy (FE-SEM) image showing protrusions of a friction layer of a fibrous triboelectric generator according to an exemplary embodiment of the present invention.

FIG. 1 is a cross-sectional view of a fibrous triboelectric generator of an exemplary embodiment of the present invention, FIG. 2 is a cross-sectional view of a fibrous triboelectric generator of another exemplary embodiment of the present invention, FIGS. 3A and 3B are schematic views of a fibrous triboelectric generator of still another exemplary embodiment of the present invention, and FIG. 4 is a field-emission scanning electron microscopy (FE-SEM) image showing protrusions of a friction layer of a fibrous triboelectric generator of an exemplary embodiment of the present invention.

Referring to FIGS. 1 to 4, the fibrous triboelectric generator 1000 of an exemplary embodiment of the present invention may include a first textile 100, a first electrode layer 200, a friction layer 300, a second electrode layer 400, and an electrical wire 500.

The first textile 100 may consist of a fibrous polymer; for example, the first textile 100 may be produced by weaving nylon (which is fibrous), but it is not limited thereto. In addition, cotton textiles, wool textiles and the like may be used as the first textile 100.

The first electrode layer 200 may be formed on a surface of the first textile, and the first electrode layer 200 may be formed by coating a surface of the first textile 100. As an example, an electrically conductive metal may be used, and gold (Au), silver (Ag), platinum (Pt), or chromium (Cr) may be used as the first electrode layer 200, but it is not limited thereto.

The friction layer 300 may be formed on a surface of the first electrode layer 200 and electrically charged by friction. The friction layer 300 may consist of a nonconductive polymer and have a surface with a concavo-convex structure. For example, the nonconductive polymer may consist of one or more selected from the group consisting of polydimethylsiloxane (PDMS), polytetrafluoroethylene (PTFE), and polyvinylidene fluoride (PVDF).

The reason for the friction layer 300 having a concavo-convex structure on a surface is to enlarge the area of the surface in which the friction layer can come into frictional contact with the second electrode layer 400 described below, and the concavo-convex structure of the surface may be exemplified as follows.

Example 1

The friction layer 300 may have a surface with a concavo-convex structure, as the surface of the friction layer 300 includes a plurality of protrusions that are spaced apart from one another.

For example, after coating a surface of the first electrode layer 200 with a nonconductive polymer to form the friction layer 300, a plurality of protrusions that are spaced apart from one another may be formed on a surface of the friction layer 300 through plasma etching of the friction layer 300 that was previously formed. In addition, a plurality of protrusions may be formed on a surface of the friction layer 300 by coating a nonconductive polymer on a surface of the first electrode layer 200 to form the friction layer 300, placing a mask with a plurality of holes thereon on a surface of the friction layer 300, injecting a nonconductive polymer into the above holes, curing the above nonconductive polymer, and then removing the above mask. As an example, the mask having one or more holes may consist of an anodic aluminum oxide (AAO) material.

Example 2

The friction layer 300 has a concavo-convex structure formed on its surface, as the surface of the friction layer 300 includes a plurality of first linear protrusions that are extended along a first direction and a plurality of second linear protrusions that are extended along a second direction which is different from the first direction.

After coating a surface of the first electrode layer 200 with a nonconductive polymer to form the friction layer 300, the above first linear protrusions and the above second linear protrusions may be formed on a surface of the friction layer 300 through an electrospinning process that spins a nonconductive polymer into a fibrous form on the surface of the friction layer 300.

The friction layer 300 may also acquire a surface with a concavo-convex structure by a different method from the above, and the different method will be described hereinafter. For this purpose, for example, the friction layer 300 may include a metal oxide 310 and a coating layer 320.

The metal oxide 310 may protrude from a surface of the first electrode layer 200. For example, a plurality of metal oxides 310 may form protrusions from the surface of the first electrode layer 200 by growing zinc oxide (ZnO) as the metal oxide 310 through a wet chemical process in a direction that is perpendicular to the surface of the first electrode layer 200.

The coating layer 320 may consist of a nonconductive polymer and coat a surface of the metal oxide 310 and the first electrode layer 200. As an example, the coating layer 320 may be formed by exposing, to a solution that contains a nonconductive polymer, the metal oxide 310, which protrudes from the surface of the first electrode layer 200, and the first electrode layer 200. For example, the coating layer 320 may be formed on the surface of the metal oxide 310 and on the first electrode layer 200 through a dip-coating process.

As an example, a nonconductive polymer may consist of one or more selected from the group consisting of PDMS, PTFE, and PVDF.

The second electrode layer 400 may undergo friction with the friction layer 300. The second electrode layer 400 may be constructed so that it can undergo friction with the friction layer 300, and for example, the friction layer 300 and the second electrode layer 400 may be made to come into frictional contact with each other by applying an external force on the second electrode layer 400 when the friction layer 300 and the second electrode layer 400 are positioned spaced apart from each other.

The second electrode layer 400 may contain an electrically conductive metal, and for example, the electrically conductive metal may be gold (Au), silver (Ag), platinum (Pt) or chromium (Cr).

According to an exemplary embodiment of the present invention, the fibrous triboelectric generator 1000 may further include a second textile 600. The second textile 600 may consist of a fibrous polymer, and for example, the second textile 600 may be produced, although not limited to, by weaving a nylon that is fibrous. In addition, the second textile 600 may be cotton textiles, wool textiles or the like.

The second textile 600 may be placed on a facing side of the first textile 100, with the second electrode layer 400 positioned therebetween, and the second electrode layer 400 may be formed on a surface of the above second textile 600. For example, the second electrode layer 400 may be formed on the surface of the second textile 600 by coating the surface of the second textile 600 with an electrically conductive metal.

As an example, when the surface of the second textile 600 consisting of a fibrous polymer is coated with a thin film of the electrically conductive metal, the second electrode layer 400 may have a surface that corresponds to the surface morphology of the second textile 600. For example, when the second textile has an embossed surface, the second electrode layer 400 may also have an embossed surface.

In this case, the area in which the friction layer 300 and the second electrode layer 400 can come into frictional contact may increase as protrusions of the second electrode layer 400 are inserted into the spaces formed among the protrusions on the surface of the friction layer 300. In addition, as the magnitude of the external force increases, the area in which the protrusions of the second electrode layer 400 are inserted into the spaces formed among protrusions that protrude from the surface of the friction layer 300 also increases, and thus the area in which the friction layer 300 and the second electrode layer 400 can come into frictional contact may increase. This will be described in detail with reference to the following FIG. 5 and FIG. 6.

When the friction layer 300 and the second electrode layer 400 come into contact with each other and then separate or when the friction layer 300 and the second electrode layer 400 come into frictional contact with each other and then separate, triboelectricity may be generated from the fibrous triboelectric generator 1000 of an exemplary embodiment of the present invention.

To enhance the electric current or voltage of the generated triboelectricity, a material that constitutes the friction layer 300 or the coating layer 320 may be suitably selected with reference to the triboelectricity series, depending on a material that makes up the second electrode layer 400.

The electrical wire 500 may electrically connect the first electrode layer 200 and the second electrode layer 400 with each other. The triboelectricity that is generated by contact or friction between the friction layer 200 and the second electrode layer 400 may move along the electrical wire 500, and the electrical wire 500 may be connected with a load.

Figure 5:
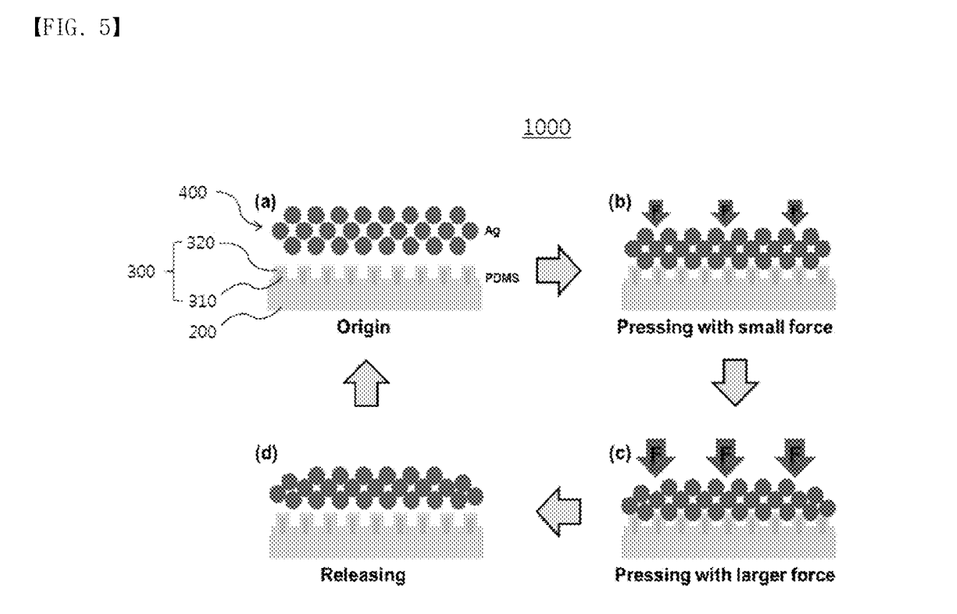
FIG. 5 is a schematic view that describes an area of contact between a friction layer and a second electrode layer for various magnitudes of an external force that is applied on a fibrous triboelectric generator of an exemplary embodiment of the present invention.
Figure 6:
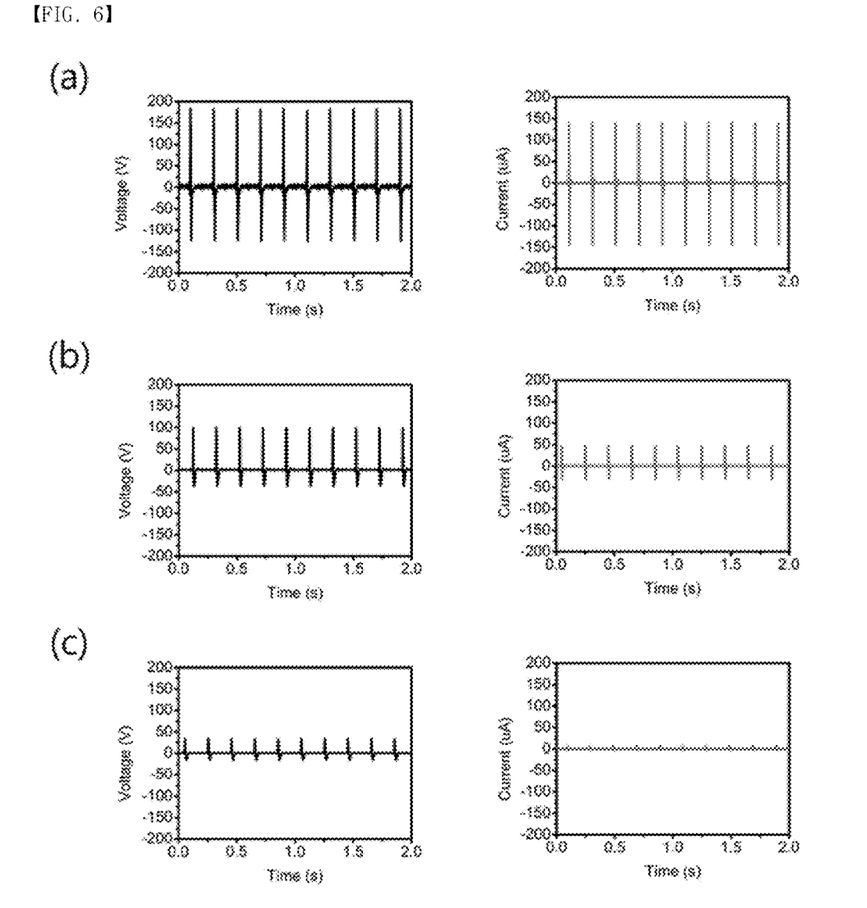
FIG. 6 is a graph showing the magnitudes of the generated voltage and electric current for various magnitudes of an external force that is applied on a fibrous triboelectric generator of an exemplary embodiment of the present invention.

FIG. 5 is a schematic view that describes an area of contact between a friction layer and a second electrode layer for various magnitudes of an external force that is applied on a fibrous triboelectric generator of an exemplary embodiment of the present invention, and FIG. 6 is a graph showing the magnitudes of the generated voltage and electric current for various magnitudes of an external force that is applied on a fibrous triboelectric generator of an exemplary embodiment of the present invention. In FIG. 6, (a) is a graph showing the magnitudes of the generated voltage and electric current when the magnitude of an external force applied on the fibrous triboelectric generator of an exemplary embodiment of the present invention is 15 kgf, (b) is a graph showing the magnitudes of the generated voltage and electric current when the magnitude of an external force applied on the fibrous triboelectric generator of an exemplary embodiment of the present invention is 5 kgf, and (c) is a graph showing the magnitudes of the generated voltage and electric current when the magnitude of an external force applied on the fibrous triboelectric generator of an exemplary embodiment of the present invention is 1 kgf.

Referring to FIG. 5, as the magnitude of the applied external force increases, the area in which the second electrode layer 400 and the friction layer 300 contact each other may also increase. This is because the protrusions of the second electrode layer 400 can be inserted into the spaces formed among the protrusions on the surface of the friction layer 300. As an area of contact increases, the magnitudes of the voltage and electric current of triboelectricity generated from the fibrous triboelectric generator 1000 of an exemplary embodiment of the present invention may also increase.

Referring to FIG. 6, it can be recognized that, as the magnitude of the external force applied on the fibrous triboelectric generator of an exemplary embodiment of the present invention decreases, the magnitudes of the generated voltage and electric current also decrease.

Example 3

Figure 7:
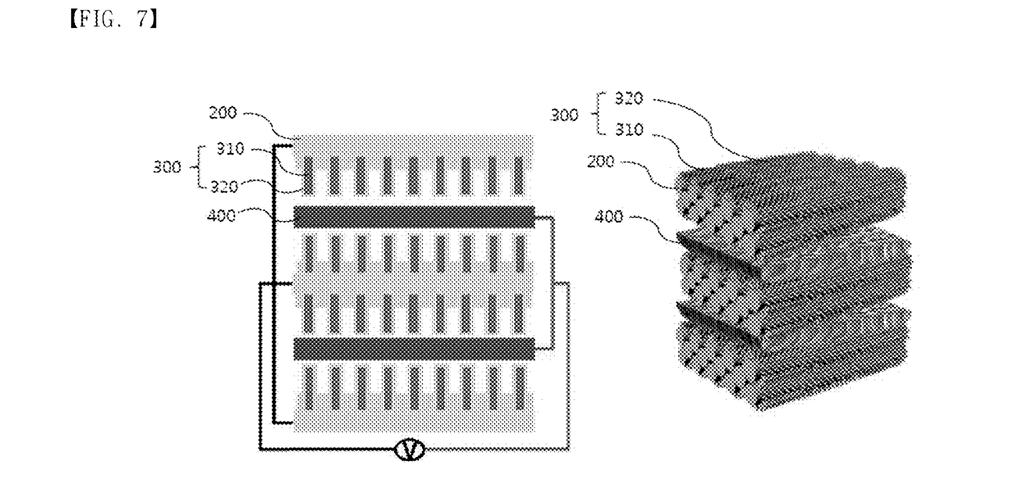
FIG. 7 is a schematic view that describes the stacking of a plurality of fibrous triboelectric generators according to an exemplary embodiment of the present invention.
Figure 8:
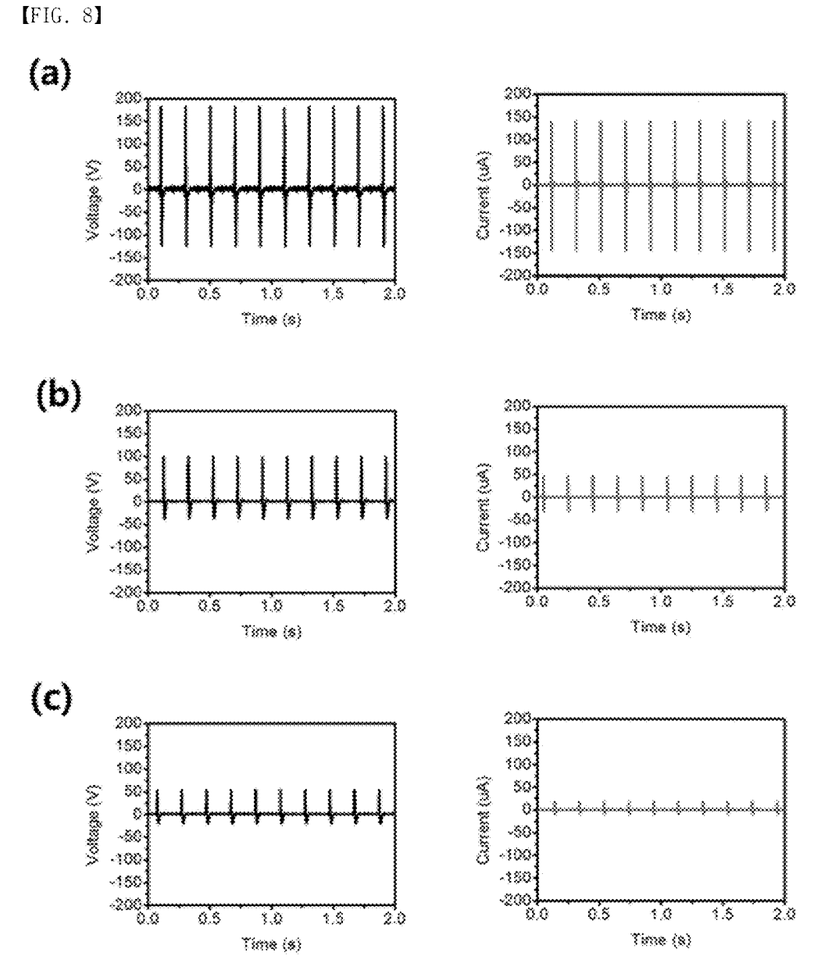
FIG. 8 is a graph showing the generated voltage and electric current for various numbers of stacked fibrous triboelectric generators of an exemplary embodiment of the present invention.

FIG. 7 is a schematic view that describes the stacking of a plurality of fibrous triboelectric generators of an exemplary embodiment of the present invention, and FIG. 8 is a graph showing the generated voltage and electric current for various numbers of stacked fibrous triboelectric generators of an exemplary embodiment of the present invention. In FIG. 8, (a) is a graph showing the voltage and electric current generated when three fibrous triboelectric generators of an exemplary embodiment of the present invention are stacked, (b) is a graph showing the voltage and electric current generated when two fibrous triboelectric generators of an exemplary embodiment of the present invention are stacked, (c) is a graph showing the voltage and electric current generated from only one fibrous triboelectric generator of an exemplary embodiment of the present invention.

Referring to FIG. 7, a plurality of the fibrous triboelectric generators 1000 may be stacked by stacking three of the fibrous triboelectric generators 1000 of an exemplary embodiment of the present invention vertically, electrically connecting the first electrode layers 200 of the fibrous triboelectric generators 1000 with one another, and electrically connecting the second electrode layers 400 of the fibrous triboelectric generators 1000 with one another. When each of the first electrode layers 200 and each of the second electrode layers 400 come into frictional contact, triboelectricity may be generated.

Referring to FIG. 8, it can be recognized that, as the number of stacked fibrous triboelectric generators 1000 decreases, the magnitudes of the generated voltage and electric current also decrease. Therefore, the user may control the magnitudes of generated voltage and electric current by controlling the number of the fibrous triboelectric generators 1000 in a stack.

Figure 9:
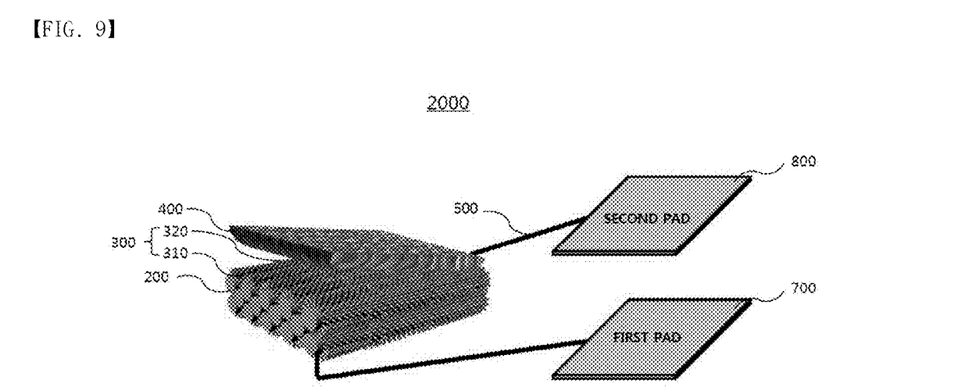
FIG. 9 is a first exemplary diagram that describes an electronic stimulator using a fibrous triboelectric generator of an exemplary embodiment of the present invention.
Figure 10:
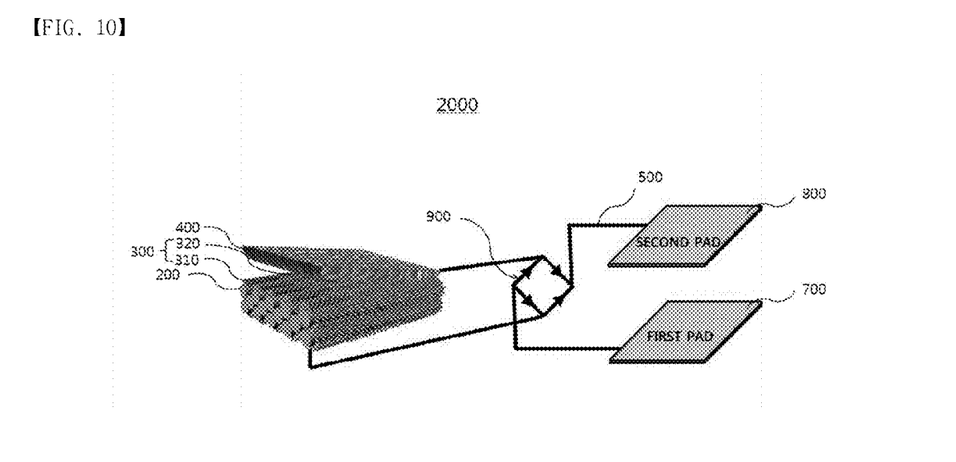
FIG. 10 is a second exemplary diagram that describes an electronic stimulator using a fibrous triboelectric generator of an exemplary embodiment of the present invention.
Figure 11:
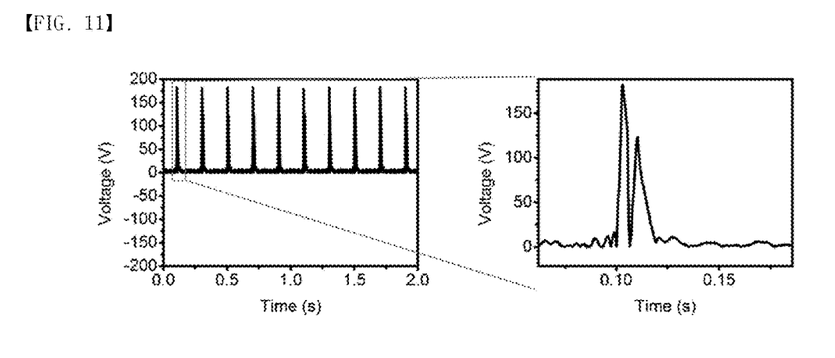
FIG. 11 is a graph that describes the voltage generated by the electronic stimulator using a fibrous triboelectric generator of FIG. 10.

FIG. 9 is a first exemplary diagram that describes an electronic stimulator using a fibrous triboelectric generator of an exemplary embodiment of the present invention, FIG. 10 is a second exemplary diagram that describes an electronic stimulator using a fibrous triboelectric generator of an exemplary embodiment of the present invention, and FIG. 11 is a graph that describes the voltage generated by the electronic stimulator using a fibrous triboelectric generator of FIG. 10.

Referring to FIG. 9, the electronic stimulator 2000 using triboelectricity according to an exemplary embodiment of the present invention may include a first textile (not shown), a first electrode layer 200, a friction layer 300, a second electrode layer 400, an electrical wire 500, a first pad 700, and a second pad 800, and referring to FIG. 10, the electronic stimulator 2000 using triboelectricity according to an exemplary embodiment of the present invention may include a first textile (not shown), a first electrode layer 200, a friction layer 300, a second electrode layer 400, an electrical wire 500, a first pad 700, a second pad 800, and a rectifier 900.

Since the first textile, the first electrode layer 200, the friction layer 300, the second electrode layer 400, and the electrical wire 500 are the same as those described with reference to FIGS. 1 to 4, detailed description thereof will be omitted.

The first pad 700 may be electrically connected with the first electrode layer 200. As an example, the first pad 700 may have a shape of a plate, exhibit electrical conductivity, consist of a flexible material, and may be configured to be detachable to a human body.

The second pad 800 may be electrically connected with the second electrode layer 400. As an example, the second pad 800 may have a shape of a plate, exhibit electrical conductivity, consist of a flexible material, and may be configured to be detachable to a human body.

When the friction layer 300 and the second electrode layer 400 come into frictional contact, the triboelectricity generated by the friction layer 300 and the second electrode layer 400 may be transferred to a human body through the first pad 700 and the second pad 800 that are attached to the human body. Electrical stimulation may be achieved, by the triboelectricity, which was transferred, stimulating the human body.

When the friction layer 300 and the second electrode layer 400 come into frictional contact, the generated triboelectricity is an alternating current, and to convert it into a direct current, the electronic stimulator 2000 using triboelectricity may further include a rectifier 900 that converts an alternating current to a direct current. As an example, a rectification diode may be used as the rectifier 900.

Referring to FIG. 11, it can be confirmed that the voltage generated from the electronic stimulator 2000 of an exemplary embodiment of the present invention, which uses triboelectricity and includes a rectifier 900, is a DC voltage.

Example 4

Figure 12:
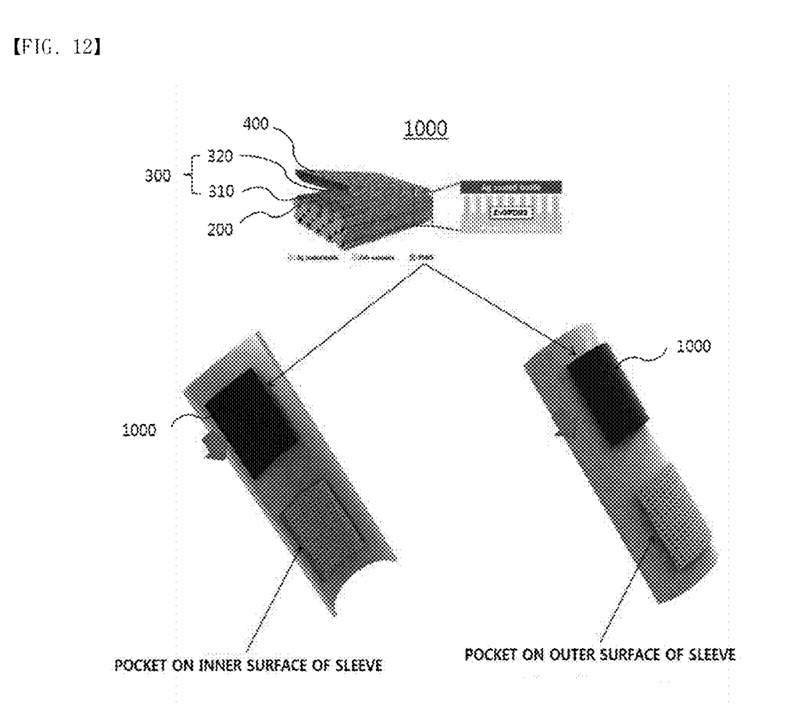
FIG. 12 is a schematic view that describes the feasibility of applying a fibrous triboelectric generator of an exemplary embodiment of the present invention in a clothes.

FIG. 12 is a schematic view that describes the feasibility of applying a fibrous triboelectric generator of an exemplary embodiment of the present invention in a clothes.

Referring to FIG. 12, the first textile 100, first electrode layer 200, and friction layer 300 of the fibrous triboelectric generator 1000 of an exemplary embodiment of the present invention may be placed to face the interior of a pocket of a clothes, and the second electrode layer 400 may be placed in the interior of the pocket of the clothes. As an example, the first textile 100 may be placed to face the interior of a pocket of a clothes, and the friction layer 300 may be placed to face the second electrode layer 400, spaced apart from each another.

The user may be able to make the friction layer 300 and second electrode layer 400 come into frictional contact by applying an external force to the pocket, and in this case, triboelectricity may be generated from the fibrous triboelectric generator 1000.

According to an exemplary embodiment of the present invention, the fibrous triboelectric generator 1000 is produced using textiles consisting of a fibrous polymer and thus can be easily applied in a clothes.

Exemplary embodiments of the present invention have been described above, and those of ordinary skill in the art will appreciate that the embodiments are only exemplary and that various modifications and equivalents of the embodiments are possible. Therefore, the true technical scope of the present invention should be defined by the appended claims.

| <Description of symbol> | |
|---|---|
| 1000: FIBROUS TRIBOELECTRIC GENERATOR | |
| 2000: ELECTRONIC STIMULATOR USING TRIBOELECTRICITY | |
| 100: FIRST TEXTILE | 200: FIRST ELECTRODE LAYER |
| 300: FRICTION LAYER | 400: SECOND ELECTRODE LAYER |
| 500: ELECTRICAL WIRE | 600: SECOND TEXTILE |
| 700: FIRST PAD | 800: SECOND PAD |
| 900: RECTIFIER | |

What is claimed is:

1. A fibrous triboelectric generator comprising:
a first textile;
a first electrode layer formed on a surface of the first textile;
a friction layer formed on a surface of the first electrode layer and configured to be electrically charged by friction, wherein a surface of the friction layer comprises first spike-shaped linear protrusions extending along a first direction from the surface of the friction layer and second spike-shaped linear protrusions extending along a second direction that is different from the first direction; and
a second electrode layer configured to generate friction with the friction layer,
wherein the friction layer consists of a nonconductive polymer.

2. The fibrous triboelectric generator of claim 1, wherein the first spike-shaped linear protrusions are spaced apart from one another.

3. The fibrous triboelectric generator of claim 2, wherein the first spike-shaped linear protrusions are formed with a space around each respective spike-shaped linear protrusion.

4. The fibrous triboelectric generator of claim 1, wherein the nonconductive polymer consists of any one or any combination of any two or more of polydimethylsiloxane (PDMS), polytetrafluoroethylene (PTFE), and polyvinylidene fluoride (PVDF).

5. The fibrous triboelectric generator of claim 1 further comprising a second textile disposed on a side facing the first textile, wherein the second electrode layer is positioned between the first textile and the second textile, and formed on a surface of the second textile.

6. The fibrous triboelectric generator of claim 5, wherein the second electrode layer is substantially planar to the second textile.

7. A fibrous triboelectric generator comprising:
a first textile;
a first electrode layer formed on a surface of the first textile;
a friction layer formed on a surface of the first electrode layer and configured to be electrically charged by friction, wherein a surface of the friction layer comprises first spike-shaped linear protrusions extending along a first direction from the surface of the friction layer; and
a second electrode layer configured to generate friction with the friction layer,
wherein the friction layer comprises:
a metal oxide forming the first spike-shaped protrusions extending from the first electrode layer; and
a coating layer coating a surface of the metal oxide and the surface of the first electrode layer.

8. The fibrous triboelectric generator of claim 7, wherein the metal oxide comprises zinc oxide (ZnO).

9. The fibrous triboelectric generator of claim 7, wherein the coating layer consists of a nonconductive polymer.

10. The fibrous triboelectric generator of claim 9, wherein the nonconductive polymer consists of any one or any combination of any two or more of polydimethylsiloxane (PDMS), polytetrafluoroethylene (PTFE), and polyvinylidene fluoride (PVDF).

11. An electronic stimulator using triboelectricity, the electronic stimulator comprising:
a first textile;
a first electrode layer formed on a surface of the first textile;
a friction layer formed on a surface of the first electrode layer, wherein a surface of the friction layer comprises first spike-shaped linear protrusions;
a second electrode layer configured to create friction in combination with the friction layer to charge the friction layer;
a first pad electrically connected with the first electrode layer; and
a second pad electrically connected with the second electrode layer,
wherein the friction layer comprises:
a metal oxide forming the first spike-shaped linear protrusions extending from the first electrode layer; and
a coating layer coating a surface of the metal oxide and the surface of the first electrode layer.

12. The electronic stimulator of claim 11, wherein the friction layer consists of a nonconductive polymer.

13. The electronic stimulator of claim 11, further comprising a second textile disposed on a side facing the first textile, wherein the second electrode layer is positioned between the first textile and the second textile and formed on a surface of the second textile.

14. The electronic stimulator of claim 11, wherein the first spike-shaped linear protrusions extend in a first direction, and the surface of the friction layer further comprises:
  second spike-shaped linear protrusions extending along a second direction that is different from the first direction.

15. A piece of clothing to generate triboelectricity, the piece of clothing comprising:
  a first textile and a second textile facing each other;
  a first electrode layer formed on a surface of the first textile and configured to be electrically charged by friction;
  a friction layer coating the first electrode layer, wherein a surface of the friction layer comprises first spike-shaped linear protrusions; and
  a second electrode layer formed on a surface of the second textile and configured to create friction in combination with the friction layer to charge the friction layer,
  wherein the first spike-shaped linear protrusions extend in a first direction, and the surface of the friction layer further comprises second spike-shaped linear protrusions extending along a second direction that is different from the first direction.

16. The piece of clothing of claim 15, further comprising:
  a first pad electrically connected with the first electrode layer; and
  a second pad electrically connected with the second electrode layer.

\* \* \* \* \*